(12) United States Patent
Drifka

(10) Patent No.: US 9,186,427 B2
(45) Date of Patent: Nov. 17, 2015

(54) METHOD AND DEVICE FOR PREVENTING CONTAMINATION FROM A DOOR WHICH OPENS VERTICALLY

(71) Applicant: Rytec Corporation, Jackson, WI (US)

(72) Inventor: Brian Norbert Drifka, Richfield, IL (US)

(73) Assignee: RYTEC CORPORATION, Jackson, WI (US)

(*) Notice: Subject to any disclaimer, the term of this patent is extended or adjusted under 35 U.S.C. 154(b) by 0 days.

(21) Appl. No.: 14/138,488

(22) Filed: Dec. 23, 2013

(65) Prior Publication Data

US 2014/0102004 A1  Apr. 17, 2014

Related U.S. Application Data

(63) Continuation of application No. 13/146,874, filed as application No. PCT/US2010/022391 on Jan. 28, 2010, now Pat. No. 8,627,605.

(60) Provisional application No. 61/206,342, filed on Jan. 28, 2009.

(51) Int. Cl.

| | |
|---|---|
| *E05D 15/38* | (2006.01) |
| *A61L 2/10* | (2006.01) |
| *E06B 9/17* | (2006.01) |
| *E06B 9/13* | (2006.01) |
| *E06B 7/16* | (2006.01) |
| *E05F 15/59* | (2015.01) |
| *E05F 15/60* | (2015.01) |

(52) U.S. Cl.
CPC . *A61L 2/10* (2013.01); *E05F 15/59* (2015.01); *E05F 15/60* (2015.01); *E06B 7/16* (2013.01); *E06B 9/13* (2013.01); *E06B 9/17046* (2013.01)

(58) Field of Classification Search
CPC ......... E06B 9/13; E06B 9/17046; E06B 7/16; E05F 15/083; E05F 15/18
USPC .......... 49/197, 199, 70, 360; 160/40, 44, 133, 160/267.1
See application file for complete search history.

(56) References Cited

U.S. PATENT DOCUMENTS

| | | | | |
|---|---|---|---|---|
| 3,115,324 | A * | 12/1963 | Chapman | 248/48.2 |
| 4,726,151 | A * | 2/1988 | Vitale | 52/16 |
| 6,176,039 | B1 * | 1/2001 | Craig | 49/26 |
| 6,247,517 | B1 * | 6/2001 | Drifka et al. | 160/23.1 |
| 7,204,291 | B2 * | 4/2007 | Last | 160/23.1 |
| 7,544,291 | B2 * | 6/2009 | Ehlers, Sr. | 210/198.1 |

(Continued)

*Primary Examiner* — Katherine Mitchell
*Assistant Examiner* — Abe Massad
(74) *Attorney, Agent, or Firm* — Factor Intellectual Property Law Group, Ltd.

(57) ABSTRACT

A door assembly including a vertically moving door to permit and prohibit access through an opening which has a top, a bottom defined by a floor, and at least two sides, the door assembly. The assembly having a door body having upper and lower portions, and being mounted proximate the opening such that the lower end portion being proximate the floor when the door is in the closed position. A protective body is configured in connection with the door so as to be moveable between a first position under at least a portion of the door body lower portion when the door is in at least a partially open position and a second storage position. The protective body having at least one debris collecting surface, and opposing ends, the protective body being configured such that debris collected on the debris collecting surface will be urged toward one of the opposed ends.

20 Claims, 7 Drawing Sheets

(56) References Cited

U.S. PATENT DOCUMENTS

| | | | |
|---|---|---|---|
| 8,627,605 B2 * | 1/2014 | Drifka | 49/197 |
| 2004/0016515 A1 * | 1/2004 | Towley | 160/133 |
| 2004/0149397 A1 * | 8/2004 | Last | 160/133 |
| 2005/0247411 A1 * | 11/2005 | Shim | 160/84.07 |
| 2010/0218431 A1 * | 9/2010 | Hardison et al. | 49/475.1 |

* cited by examiner

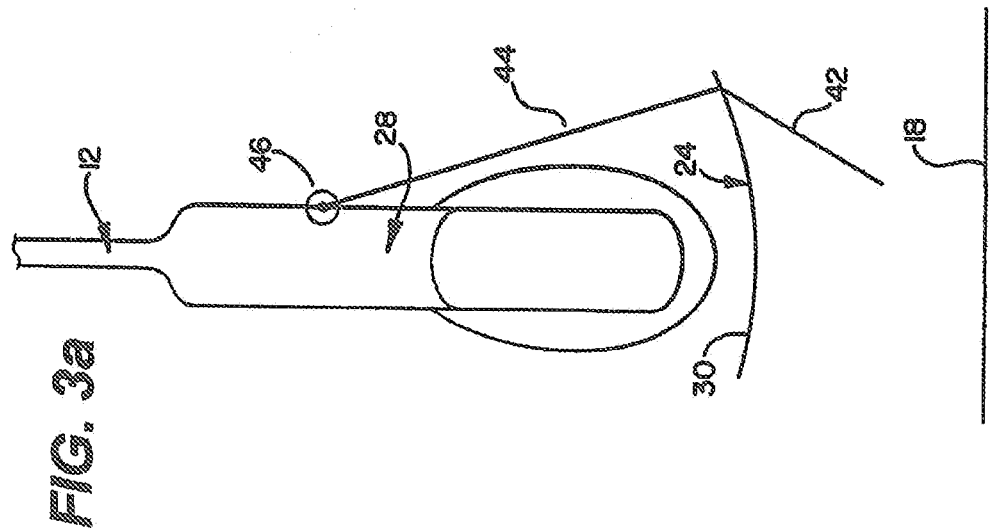
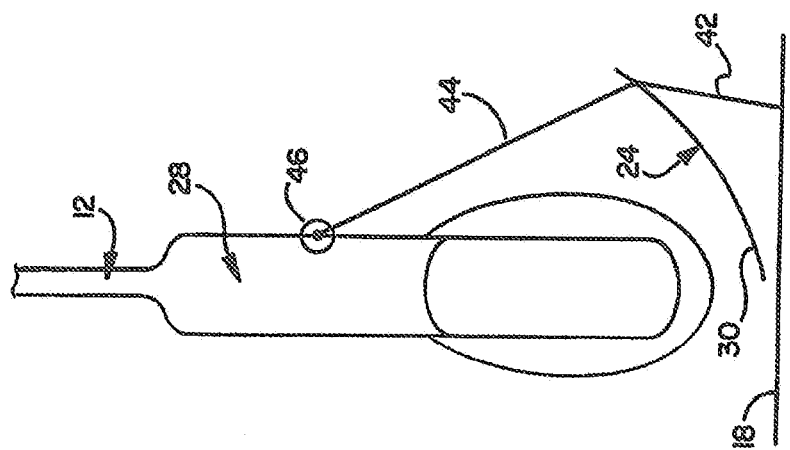
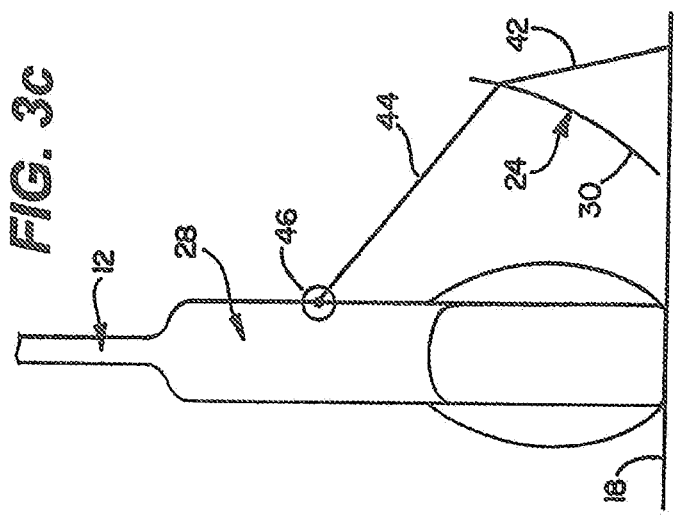

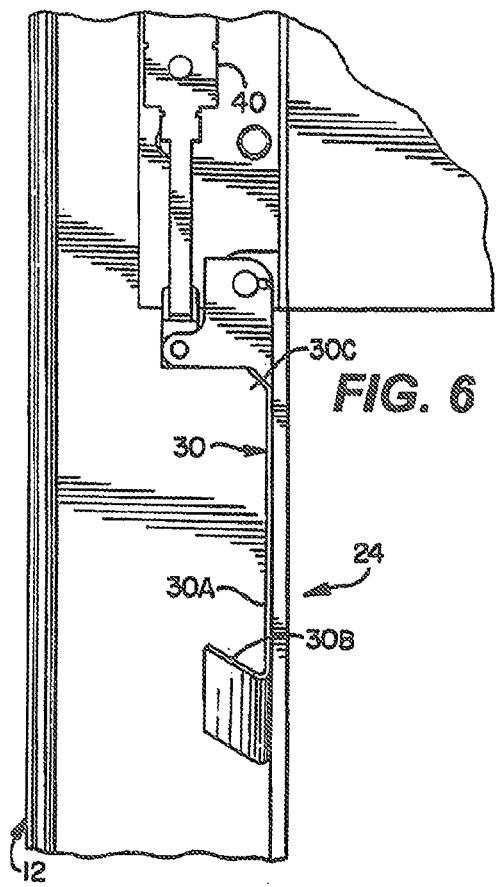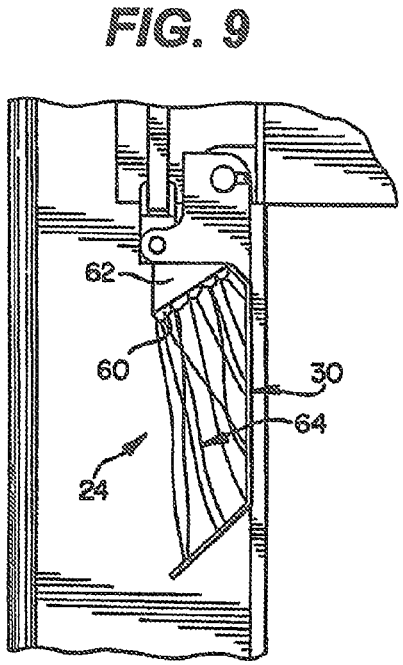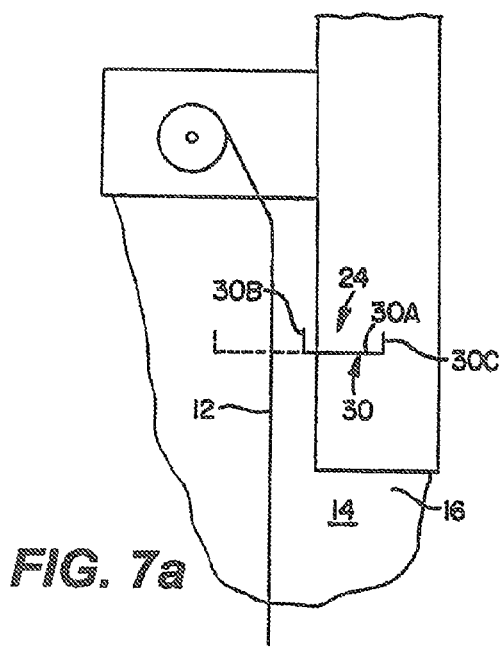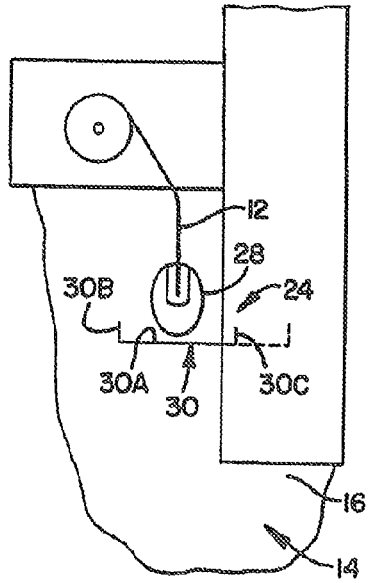

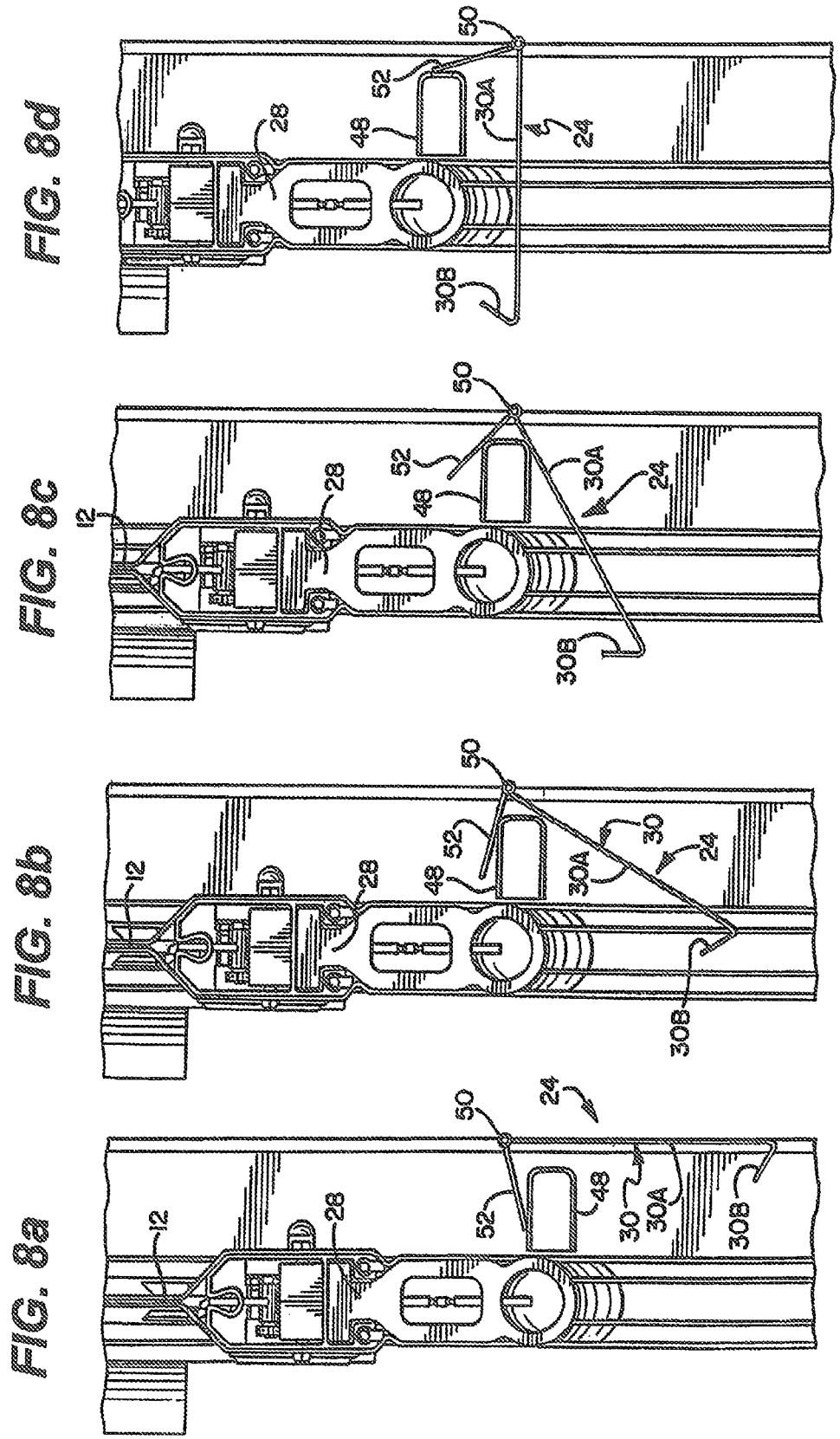

METHOD AND DEVICE FOR PREVENTING CONTAMINATION FROM A DOOR WHICH OPENS VERTICALLY

CROSS REFERENCE TO RELATED APPLICATIONS

This application is a continuation of U.S. patent application Ser. No. 13/146,874 filed Jul. 28, 2011 which claims the filing benefit of International Patent Application No. PCT/US2010/022391, filed Jan. 28, 2010, which claims priority to U.S. Provisional Patent Application Ser. No. 61/206,342, filed Jan. 28, 2009, the contents of all of which are incorporated herein by reference.

TECHNICAL FIELD

The present invention relates to a door assembly which opens and closes vertically, and more specifically, to means for preventing debris falling from a lower portion of the door when the door is in an at least partially open position.

BACKGROUND OF THE INVENTION

Overhead-doors are typically sealed by contacting a lower portion, typically the bottom edge portion of the door, and perhaps a seal, with the floor. However in many applications this can pose a problem where debris is located on the floor beneath the door because, when the door is closed against the floor, the bottom of the door and/or seal can come into contact with the debris. Also, debris in many forms including condensed moisture can contaminate the lower portion of the door by various means. Accordingly, when the door is opened, there is the potential for this debris to fall from the bottom portions or leading edge of the door and/or seal onto objects (e.g. food) and/or people passing through the doorway.

In order to prevent such debris from falling onto objects and/or people passing beneath the door, the Applicant of this invention has previously provided a protective body consisting of essentially a collection surface connected to a pneumatic cylinder. When the door is fully opened, the protective body substantially spans the width of the door and collects debris that falls while the door is fully open. When using this protective body however, as the door begins to close, the protective body is rotated from a position where the collection surface is substantially horizontal to the floor to a position that is substantially perpendicular to the floor. This leads to a situation where debris collected on the protective body will drop onto objects and/or people or the floor below when the guard is moved out of the path of the door. So while protection of contamination by debris dropping is provided during the fully open time of the door, during opening and closing, where traffic may still be in the door opening, contamination may occur. The present invention is directed towards structures and methods to solve these deficiencies and to provide new advantages in prevention of contaminating cargo or persons traversing the opening or passage while the door is still overhead.

BRIEF DESCRIPTION OF THE DRAWINGS

FIGS. 3A-3C partial side plan views of the door of FIG. 1 exemplifying the progression of movement of a protective body according to the invention;

FIG. 6 is a partial plan view of an embodiment of the present invention;

FIGS. 7A-7B are schematic side views showing a door according to the invention in relatively opened and closed positions;

FIGS. 8A-8D are partial side plan views exemplifying a progression of movement for an embodiment of the present invention; and, FIG. 9 is a schematic side in partial of another embodiment of the present invention.

DETAILED DESCRIPTION

Figure 1:
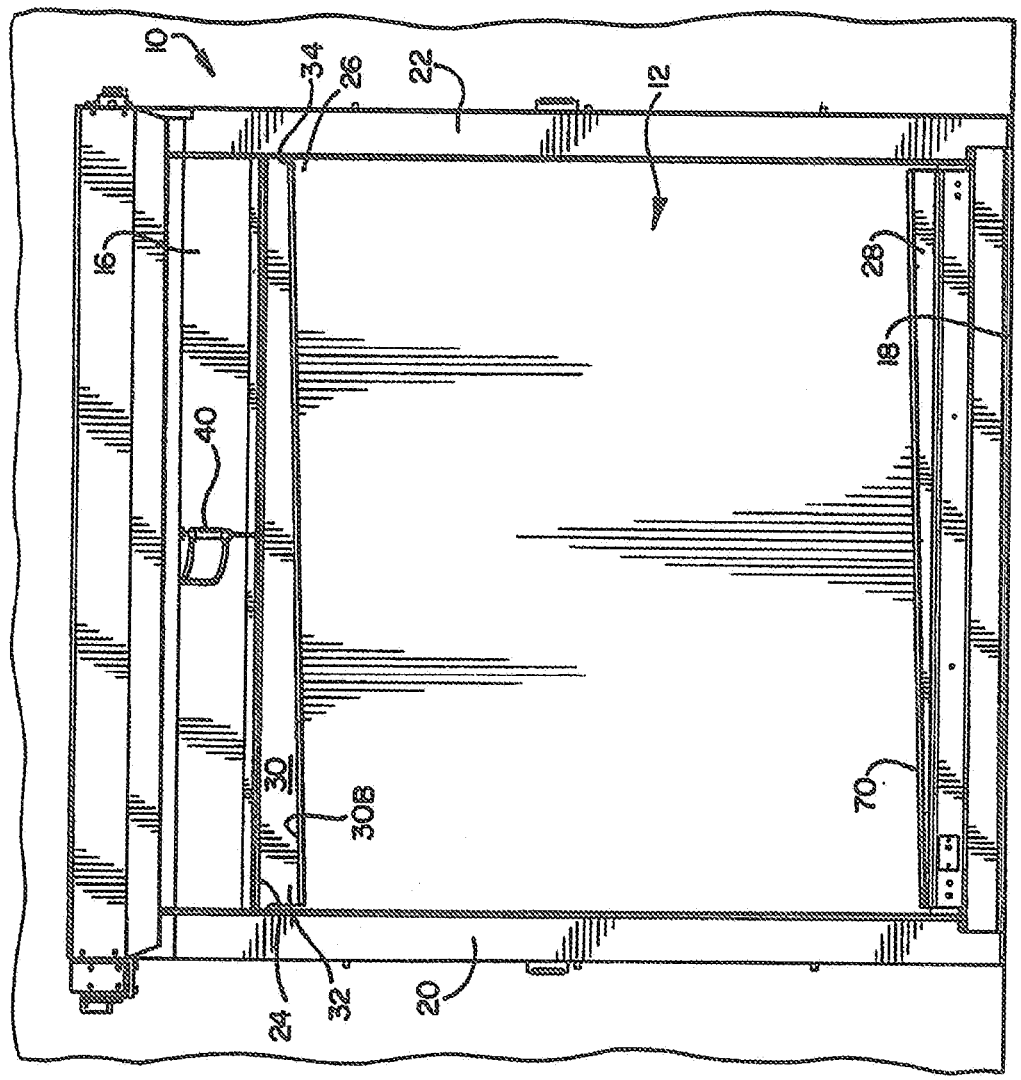
FIG. 1 is a front plan view exemplifying an embodiment of the present invention when the door is in a fully closed position.

While the present invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

FIG. 1 discloses a high-speed door assembly 10 of the present invention. It will be appreciated by those of skill in the art that the present invention will also provide benefits for vertically moving doors which are neither high speed nor operated by motors or automated open/close circuitry.

Figure 2:
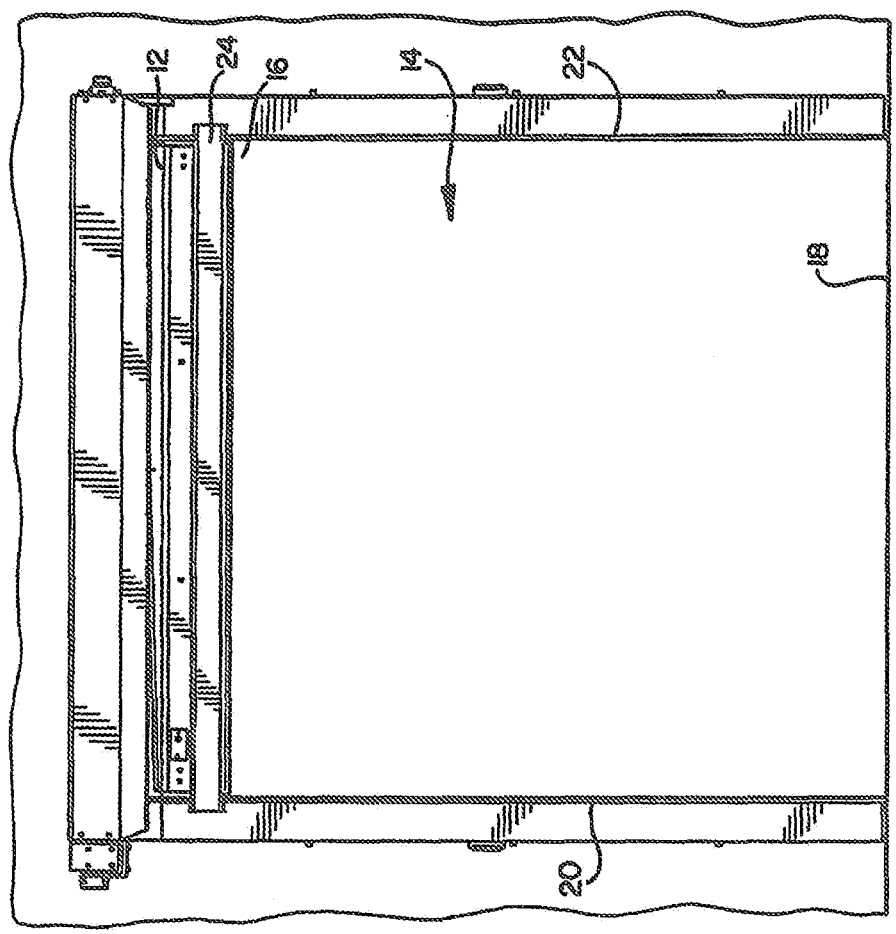
FIG. 2 is a front plan view exemplifying the embodiment of FIG. 1 when the door is in the fully open position.

As disclosed in FIG. 2 assembly 10 includes a vertically moving door, having a door body 12, that permits and prohibits access through a door opening 14. Opening 14 is defined by a top 16, a bottom defined by a floor 18, and at least two sides 20, 22. Assembly 10 also includes a protective body 24.

A disclosed in FIG. 1, the door body 12 has an upper end 26 and a lower end 28. When the door body 12 is in a closed position, the lower end 28 is located proximate the floor 18. In this position the lower end 28 of the door body 12 may contact and pick up debris in the form of solid or liquid. In applications where door body 12 separates areas of differing temperature and or humidity, the lower portion 28 may also have frost or sweat from the atmosphere as "debris." Consequently, when in the door body 12 is in a partially open position this debris may fall onto objects and/or people passing through the opening 14 below.

In order to prevent the debris from falling on objects and/or people as they pass through the opening 14, the door assembly 12 includes a protective body 24. The protective body 24 may be located proximate the top of the opening 14, as shown in FIGS. 1 and 2, or attached proximate the lower end 28 of the door body 12, as shown in FIGS. 3A-3C, or anywhere in between.

The protective body 24 comprises at least one debris collecting surface 30 and opposing ends 32, 34 and is configured so as to be moveable between a first position under at least a portion of the door body lower end 28, when the door body 12 is in at least a partially open position as disclosed in FIG. 2, and a second storage position as disclosed in FIG. 1. Stated another way, when the debris collecting surface 30 is in the first position, it is positioned such that any debris falling from the door body 12 is "caught" or collected by the surface and therefore prevented from falling onto the ground, or any people and/or objects below. As seen in FIG. 1, the protective body 24 is configured such that debris in the form of liquid or solid collected on the debris collecting surface 30 will be urged toward one side 20 or 22 of the opening 14.

Figure 4:
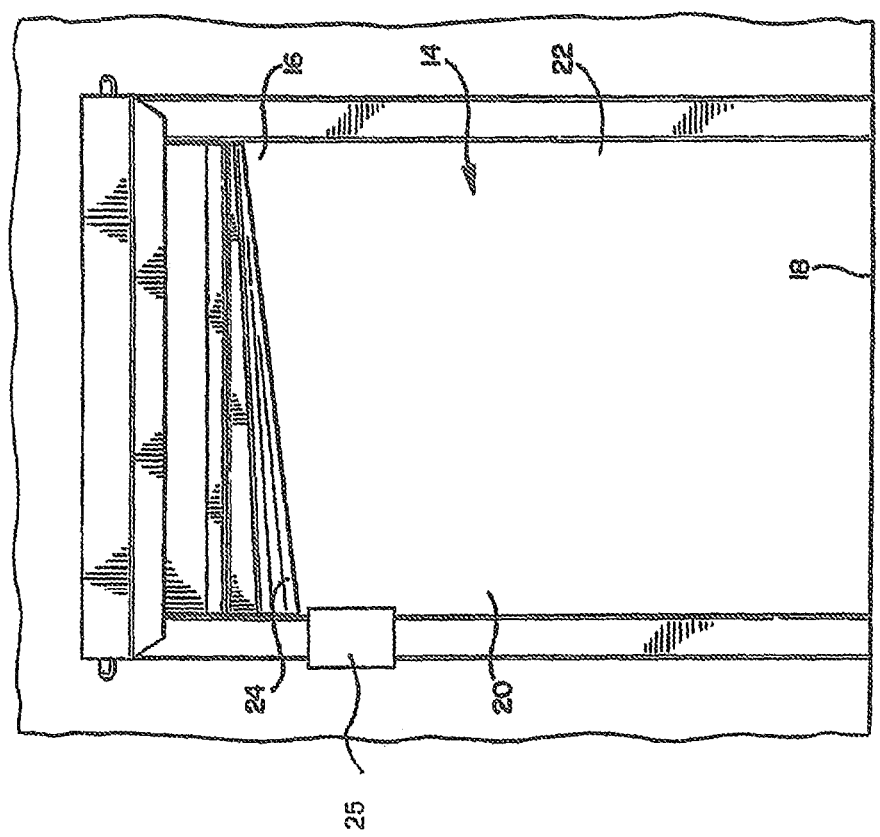
FIG. 4 is a front plan view of a door having an embodiment similar to FIG. 1 but with a steeper angle employed on a protective body according to the invention.
Figure 5A:
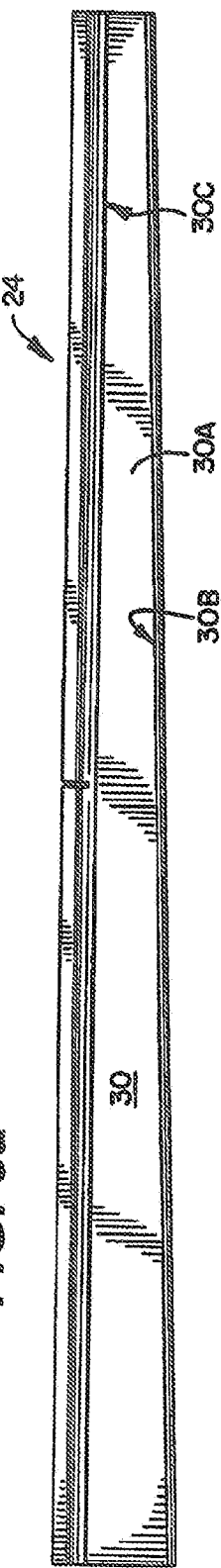
FIG. 5A-5C show various views of an embodiment of a protective body according to the present invention.
Figure 5B:
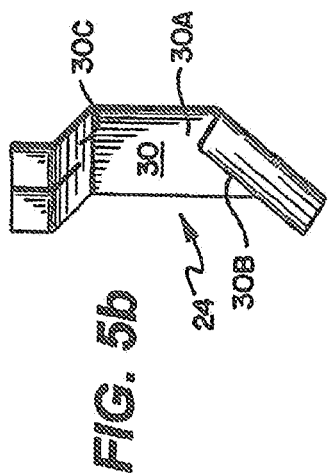
Figure 5C:
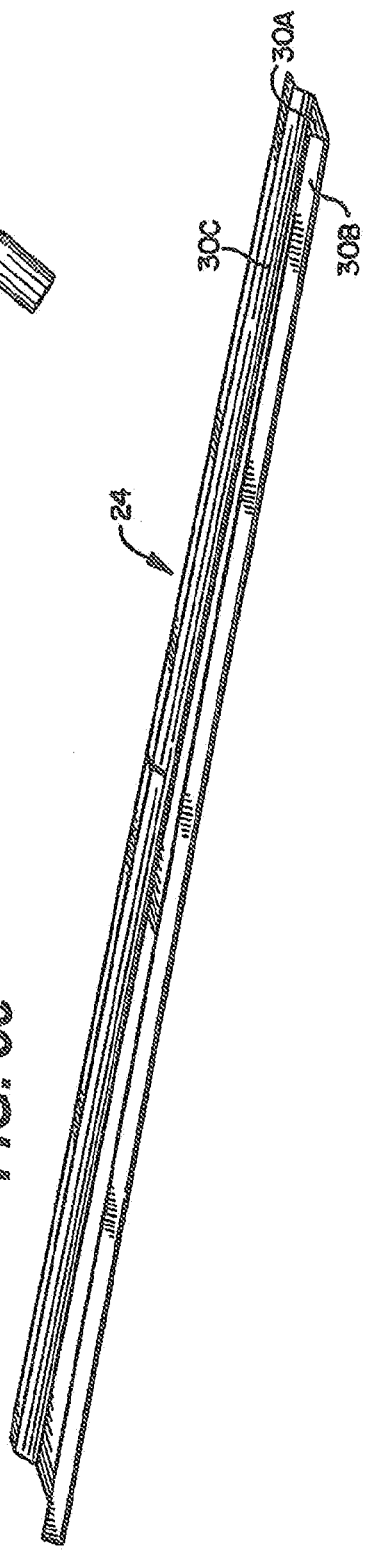

The urging of fallen debris once collected on the protective body 24 towards one side can be accomplished by canting a portion of the protective body 24, as shown in FIG. 1. Canting a portion the protective body allows gravity to facilitate the movement of debris from one end of the protective body 24 towards the other end of the protective body 24 when in the second position. In an alternative embodiment, a container (see for example container 25 in FIG. 4 which may also be incorporated into the door assembly shown in FIG. 1) may be provided under the lower end of protective body 24 allowing debris to enter the container. In any embodiment, it should be appreciated that by canting different portions of the protective body 24, gravity can facilitate the movement of debris when the protective body 24 is in the first position as well, as shown in FIG. 4.

The canting portion of the protective body 24 can be provided by dividing the debris collecting surface 30 into various portions creating an angled surface such as surface 30B. As shown, e.g. in FIGS. 5A-C and 6, the canting of the protective body 24 can be accomplished by dividing the debris collecting surface 30 into three separate portions 30A, 30B, and 30C. As shown, in FIGS. 5A-C and 6, the canted portion 30B of the debris collecting surface 24 is substantially horizontal to the ground in the first position, as shown e.g. in FIG. 2 where surface 30B is on the opposite side of 30C, and is thus only canted towards one end when the protective body is in the second position, shown in, for e.g., FIGS. 1, 5A-C, and 6.

The protective body 24 can be either rotationally (shown e.g. FIGS. 1, 2, 3A-C) or translationally (shown in FIGS. 7A and 7B) moved from the first to the second position. In embodiments where the protective body 24 is translationally moved from the first to second position in a substantially horizontal fashion, as shown in FIGS. 7A and 7B, it should be appreciated by those in the art that there is no need to provide a canted a portion of the protective body 24. When using a translation movement, the debris collecting surface 30 remains substantially horizontal to the floor and therefore does not allow debris to fall in either the first or second position. As such, canting a portion of the protective body 24 to prevent debris from falling when in the second position is superfluous as the second position in such an embodiment does not facilitate the movement of debris towards the floor.

In order to facilitate the movement of the protective body, an actuator is used. As shown in FIGS. 1 and 6, the actuator may be a hydraulic cylinder 40 rotating the protective body 24. However it should be appreciated that the actuator can also be a solenoid, a linear variable differential transformer, or any similar devices which can facilitate the movement of the protective body 24. When using an electronic actuator, it should be appreciated by those in the art that an electronic controller can be used to control the electronic device moving the protective body 24 between the first and second positions and that such a controller can be logistically coordinated with an automated door control system.

In an alternative embodiment, shown in FIGS. 3A-C, the combination of a mechanical arm 42 attached to the protective body 24 and gravity can provide suitable actuation. In this alternative embodiment, the protective body 24 is attached proximate the lower end 28 of the door body 12 via swing arm 44 pivotable around a pivot point 46. As shown in FIG. 3A, attaching protective body 24 in such a manner allows protective body to remain in the first position underneath the lower end 28 of door body 12 during substantially the entire opening/fully open/closing cycle. As shown in FIG. 3B, as the lower end 28 of the door body 12 approaches the bottom of the opening defined by the floor 18, mechanical arm 42 contacts the floor 18 causing the protective body 24 to lift and rotate out of the way of door body 12 so as to permit the door body edge portions to seal against the floor 18. It should be appreciated by those of skill in the art that other mechanical means, e.g. wheels, additional pivot points, etc., can be used either alone or in conjunction with the mechanical arm 42 to move protective body 24 as door body 12 closes. When the door body 12 is in the fully closed position, shown in FIG. 3C, the protective body 12 is substantially held off the floor 18 by mechanical arm 42. This embodiment has the added advantage of not only protecting objects and/or people as they pass through the opening, it also has the advantage of preventing any debris from falling to the floor in the opening as the door opens and closes creating a safer passageway.

In yet another embodiment of the present invention, shown in FIGS. 8A-D, the combination of a surface 48, gravity, and pivot point 50 can provide suitable actuation to move the protective body 24. As shown in FIGS. 8A-D, a surface 50 is attached proximate the lower end 28 of door body 12. As door body 12 approaches the top 16 of opening 14, the surface 50 engages portion 52 of the debris collecting surface 30. The surface 48 attached to the lower end 28 is positioned such that when door body 12 is in the fully open position, the surface 48 remains engaged with protective body 12, thereby holding the protective body 24 in the first position underneath door body 12. In such an embodiment, as the door body 12 is lowered, the surface 48 disengages, releasing the protective body 24, allowing it to return to the second position, out of the path of the door body 12.

Since some environments and applications of vertically moving doors, require higher standards of cleanliness, it may be desirable to treat collected debris that may not be removed by a canting of a collection surface. To meet this requirement, the high-speed door assembly 10 may further be provided with means for reducing bacterial or viral growth. One such means is disclosed as ultra-violet light source 60 shown in FIG. 9. The ultra-violet light source 60 can be attached directly to the protective body 24 or a light attachment surface 62 may be attached to the protective body 24. Using either attachment method, the ultra-violet light source 60 should be attached in a manner that allows the emitted ultra-violet light 64 to impinge on at least a portion of collected debris on the debris collecting surface 30. The ultra-violet light source 60 may take the form of light-emitting diodes, which can be operated using either direct-current or alternating-current.

The high-speed door assembly 10 may further include a second protective body 70 for collecting liquid run-off from condensation on the door body 12. The second protective body 70 is preferably attached proximate the lower end 28, as shown in FIG. 1. As shown in FIG. 1, the second protective body 70 is canted from one end towards its other end so gravity facilitates the movement of liquid debris towards the lower end. As shown in FIG. 1, in embodiments without a container to collect fluids or other debris, it can be advantageous for the canted end of the second protective body 70 to be located on the same side of opening 14 as protective body 24. This allows for easier clean up, as debris will all collect on one side of opening 14.

It is to be understood that additional embodiments of the high-speed door assembly described herein may be contemplated by one of ordinary skill in the art and that the scope of the present invention is not limited to the embodiments disclosed. While specific embodiments of the present invention have been illustrated and described, numerous modifications come to mind without significantly departing from the spirit of the invention, and the scope of protection is only limited by the scope of the accompanying claims.

We claim:

1. A door assembly to permit and prohibit access through an opening, the door assembly comprising:
   a door body having a lower edge, the door body being mounted proximate the opening such that the door body may be moved vertically to open and close the opening such that the lower edge is positioned proximate a lower boundary of the opening when the door body is in a closed position;
   a protective body configured to be moveable between a first position under the lower edge of the door body when the door body is in at least a partially open position, and a second storage position;
   the protective body having at least one debris collecting surface, and opposing ends, the protective body being configured such that debris collected on the debris collecting surface will be urged toward one of the opposing ends.

2. The door assembly of claim 1 wherein the protective body is located proximate a top portion of the opening.

3. The door assembly of claim 1 wherein the protective body is attached proximate the lower edge of the door body.

4. The door assembly of claim 1 wherein at least a portion the protective body is canted from one of its opposing ends towards the other so gravity facilitates the movement of debris towards one side of the opening when the protective body is in the second storage position.

5. The door assembly of claim 1 wherein the protective body moves rotationally between the first position and the second storage position.

6. The door assembly of claim 1 wherein the protective body moves translationally between the first position and the second storage position.

7. The door assembly of claim 1 further comprising an actuator for moving the protective body between the first position and the second storage position.

8. The door assembly of claim 7 wherein the actuator for moving the protective body is at least one from the group of: a hydraulic cylinder, a solenoid, and a linear variable differential transformer.

9. The door assembly of claim 8 having wherein the actuator for moving the protective door which is controlled by an electronic controller.

10. The door assembly of claim 7 wherein the actuator is an arm attached to the protective body.

11. The door assembly of claim 8 wherein the actuator is a body attached proximate the lower edge of the door body.

12. The door assembly of claim 1 further comprising a container located such that when the protective body is in the second position, debris may enter the container.

13. The door assembly of claim 1 further comprising an ultra-violet light source situated such that ultra-violet light therefrom impinges on at least a portion of collected debris.

14. The door assembly of claim 13 wherein the ultra-violet light source is at least one light-emitting diode.

15. The door assembly of claim 13 wherein the ultra-violet light source is attached directly to the protective body.

16. The door assembly of claim 1 further comprising a second protective body having opposing ends and being non-moveably attached proximate the lower edge of the door body.

17. The high-speed door assembly of claim 16 wherein the second protective body is canted from one end towards its other end so gravity facilitates the movement of liquid debris from one of the opposing ends to the other.

18. The high-speed door assembly of claim 17 wherein the protective body and the second protective body are canted in such a manner as to facilitate the movement of debris in the same direction.

19. A door assembly to permit and prohibit access through an opening, the door assembly comprising:
   a door body mounted proximate the opening such that the door body may be moved vertically to open and close the opening such that a lower edge of the door body contacts a lower boundary of the opening when the door body is in a closed position;
   a protective body configured to be moveable between a first position under at least a portion of the lower edge of the door body when the door body is in at least a partially open position, and a second storage position;
   the protective body having at least one debris collecting surface, and opposing ends, the protective body being configured such that debris collected on the debris collecting surface will be urged toward one of the opposing ends in at least one of the first position and the second storage position.

20. The door assembly of claim 19 wherein the protective body extends horizontally across substantially an entire width of the opening.

* * * * *